(12) United States Patent  
Cingone (10) Patent No.: US 9,427,648 B2
(45) Date of Patent: Aug. 30, 2016

(54) DYNAMIC TRAINING APPARATUS (71) Applicant: James Cingone, Setauket, NY (US)

(72) Inventor: James Cingone, Setauket, NY (US)

( * ) Notice: Subject to any disclaimer, the term of this patent is extended or adjusted under 35 U.S.C. 154(b) by 71 days.

(21) Appl. No.: 14/303,630

(22) Filed: Jun. 13, 2014

(65) Prior Publication Data

US 2015/0360109 A1 Dec. 17, 2015

(51) Int. Cl.
A63B 69/00 (2006.01)
A63B 24/00 (2006.01)
A63B 71/02 (2006.01)

(52) U.S. Cl.
CPC ....... *A63B 69/0097* (2013.01); *A63B 24/0075* (2013.01); *A63B 69/0053* (2013.01); *A63B 71/023* (2013.01); *A63B 2024/004* (2013.01); *A63B 2071/025* (2013.01); *A63B 2220/53* (2013.01); *A63B 2220/62* (2013.01); *A63B 2220/801* (2013.01); *A63B 2225/09* (2013.01); *A63B 2225/50* (2013.01)

(58) Field of Classification Search
USPC .............. 473/435, 478, 447; 273/407; 463/2
See application file for complete search history.

(56) References Cited

U.S. PATENT DOCUMENTS

| | | | |
|---|---|---|---|
| 3,158,372 A | 11/1964 | Ohlund et al. | |
| 3,160,228 A * | 12/1964 | De Witt Steed | .......... E04G 1/22 108/147 |
| 3,180,643 A | 4/1965 | Kallai | |
| 3,349,620 A | 10/1967 | Speiser | |
| 3,427,026 A | 2/1969 | Mahoney | |
| 3,655,202 A | 4/1972 | Gautraud et al. | |
| 3,659,850 A | 5/1972 | Psenka | |
| 3,692,307 A | 9/1972 | Henry | |
| 3,711,092 A | 1/1973 | Hogue | |
| 3,752,476 A * | 8/1973 | Mahoney | ............. A63B 9/0097 248/156 |
| 3,836,144 A | 9/1974 | Mahoney | |
| 3,963,240 A | 6/1976 | Tidwell | |
| 3,994,107 A | 11/1976 | Aughuet | |
| 4,070,018 A | 1/1978 | Hodges | |
| 4,082,271 A | 4/1978 | Martin | |
| 4,093,218 A | 6/1978 | Burchers | |
| 4,116,437 A | 9/1978 | Johnson | |
| 4,191,374 A | 3/1980 | Kulesza et al. | |
| 4,202,543 A * | 5/1980 | Collins | .................. A63C 19/00 273/359 |
| 4,210,326 A | 7/1980 | Booth et al. | |
| 4,239,235 A | 12/1980 | Torres | |
| 4,257,594 A | 3/1981 | Conrey et al. | |
| 4,309,032 A | 1/1982 | Facius | |
| 4,330,129 A | 5/1982 | Meredith | |
| D265,413 S | 7/1982 | Millikan | |

(Continued)

FOREIGN PATENT DOCUMENTS

CN 203208631 U 9/2013

OTHER PUBLICATIONS

Webpage download, Youtube2009, 2009, www.youtube.com/watch?v=SOESSCXGhFo, 3 pages.*

*Primary Examiner* — Gene Kim
*Assistant Examiner* — M Chambers
(74) *Attorney, Agent, or Firm* — Carter, DeLuca, Farrell & Schmidt, LLP (57) ABSTRACT

A dynamic training apparatus includes a platform, a first motor, a moving assembly, and a rebound wall. The moving assembly is coupled to the platform and the first motor and is movable in response to an actuation of the first motor. The rebound wall is coupled to the moving assembly and is pivotable relative to the platform in response to movement of the moving assembly.

17 Claims, 11 Drawing Sheets

(56) References Cited

U.S. PATENT DOCUMENTS

| | | |
|---|---|---|
| 4,373,720 A | 2/1983 | Lombardi et al. |
| 4,417,728 A | 11/1983 | Hay et al. |
| 4,421,318 A | 12/1983 | Sverdlik et al. |
| 4,456,251 A | 6/1984 | Balaz |
| 4,482,156 A | 11/1984 | Karlsson |
| 4,491,321 A | 1/1985 | Veenema |
| 4,522,394 A * | 6/1985 | Broussard .............. A63B 71/02 188/72.8 |
| 4,546,984 A | 10/1985 | Towle et al. |
| 4,630,832 A | 12/1986 | Swanson |
| 4,807,879 A | 2/1989 | Eliot |
| 4,905,996 A | 3/1990 | Tallent et al. |
| 4,943,056 A | 7/1990 | Bowers |
| 4,971,335 A | 11/1990 | Galvin |
| 4,995,607 A | 2/1991 | Whitfield |
| 5,039,109 A * | 8/1991 | Mahoney ........... A63B 69/0097 248/647 |
| 5,336,959 A * | 8/1994 | Park ...................... H02N 2/183 310/328 |
| 5,342,063 A | 8/1994 | O'Brien et al. |
| 5,403,017 A | 4/1995 | Doss, III et al. |
| 5,407,211 A | 4/1995 | Bottiglieri |
| 5,419,565 A | 5/1995 | Gordon et al. |
| 5,516,113 A | 5/1996 | Hodge |
| 5,553,860 A | 9/1996 | Zelikovich |
| 5,573,239 A | 11/1996 | Ryker et al. |
| 5,613,922 A | 3/1997 | Hsiang |
| 5,642,879 A | 7/1997 | Rodriguez |
| 5,772,537 A | 6/1998 | Anderson et al. |
| 5,779,241 A | 7/1998 | D'Costa et al. |
| 5,833,234 A | 11/1998 | Vavala et al. |
| 5,848,791 A | 12/1998 | Beyer et al. |
| 5,857,679 A | 1/1999 | Ringe et al. |
| 6,209,877 B1 | 4/2001 | Warnick |
| 6,299,554 B1 | 10/2001 | Sinclair et al. |
| 6,422,956 B1 | 7/2002 | Kusmiss |
| 6,551,205 B1 | 4/2003 | Koelzer, Jr. et al. |
| 6,880,828 B2 | 4/2005 | Liao |
| 6,935,971 B2 | 8/2005 | Piras et al. |
| 7,201,675 B2 | 4/2007 | Morrison |
| 7,249,767 B1 | 7/2007 | Gorton |
| 7,427,069 B2 | 9/2008 | Bateman et al. |
| 7,662,053 B1 | 2/2010 | Summers et al. |
| 7,677,993 B2 | 3/2010 | McTavish |
| 7,713,149 B2 | 5/2010 | Docherty |
| 7,805,276 B1 | 9/2010 | Byers et al. |
| 7,950,666 B2 | 5/2011 | Stincelli et al. |
| 7,998,003 B2 | 8/2011 | Orr |
| 7,999,694 B2 * | 8/2011 | Martin ...................... F41J 5/02 340/323 R |
| 8,016,700 B2 | 9/2011 | McTavish et al. |
| 8,043,172 B2 | 10/2011 | Campanaro et al. |
| 2002/0098921 A1 | 7/2002 | Parkinson et al. |
| 2003/0060309 A1 | 3/2003 | Smith |
| 2003/0190981 A1* | 10/2003 | Walker, Jr. ......... A63B 69/0071 473/447 |
| 2007/0024006 A1 | 2/2007 | Marshall et al. |
| 2007/0117068 A1* | 5/2007 | Nelms ..................... G09B 9/02 434/29 |
| 2008/0164657 A1 | 7/2008 | Sheldon |
| 2008/0258394 A1 | 10/2008 | Allingham |
| 2008/0261727 A1 | 10/2008 | Snyder |
| 2009/0014961 A1 | 1/2009 | Bateman et al. |
| 2009/0069125 A1 | 3/2009 | Porter |
| 2009/0163303 A1 | 6/2009 | Prince |
| 2009/0191384 A1 | 7/2009 | Jones |
| 2010/0032906 A1 | 2/2010 | Wilcox |
| 2010/0062880 A1 | 3/2010 | Hayes |
| 2010/0093471 A1 | 4/2010 | Huang |
| 2010/0125009 A1 | 5/2010 | Goldwitz |
| 2010/0173732 A1 | 7/2010 | Vaniche et al. |
| 2010/0227714 A1 | 9/2010 | Fittler |
| 2010/0285905 A1 | 11/2010 | Guttler |
| 2010/0292033 A1 | 11/2010 | Sarver |
| 2011/0037039 A1* | 2/2011 | Li ............................. B66F 3/22 254/122 |
| 2011/0037227 A1 | 2/2011 | O'Neal et al. |
| 2011/0053713 A1 | 3/2011 | Bulloch |
| 2011/0062668 A1 | 3/2011 | Leimberer |
| 2011/0068538 A1 | 3/2011 | Kuyl |
| 2011/0163504 A1 | 7/2011 | Berger et al. |
| 2011/0175294 A1 | 7/2011 | Amodt |
| 2015/0306455 A1* | 10/2015 | DeCarlo ................ A63B 24/00 473/422 |
| 2015/0360109 A1* | 12/2015 | Cingone ............ A63B 69/0097 473/435 |

* cited by examiner

FIG. 10

DYNAMIC TRAINING APPARATUS

TECHNICAL FIELD

The present disclosure relates to dynamic training apparatus for use in athletic activities. More specifically, the present disclosure relates to movable walls that act as dynamic surfaces upon which a ball, e.g., a tennis ball, can be hit against and returned. Methods of operating the movable walls are also described.

BACKGROUND

Contacting or throwing/tossing a round object or ball is an integral part of certain sports, e.g., tennis, baseball, lacrosse, and soccer. Participants of such sports often seek to improve their skills by repeatedly hitting or throwing/tossing balls against a stationary wall. The stationary wall, which generally has a planar surface fabricated from a hard material, such as, for example, concrete, extends perpendicularly upwardly from the ground to return balls to the participant after the balls make contact therewith.

However, various drawbacks exist with the above-described stationary walls. For example, stationary walls return balls to the participant in a manner that can be easily predicted and controlled by the participant, making training with the stationary walls ineffective and less desirable for advanced athletes.

Accordingly, a need exists for a training apparatus that returns balls in a less predictable manner.

SUMMARY

According to an aspect of the present disclosure, an embodiment of a dynamic training apparatus is provided. The dynamic training apparatus includes a platform, a first motor, a moving assembly, and a rebound wall. The moving assembly is coupled to the platform and the first motor. The moving assembly is movable in response to an actuation of the first motor. The rebound wall is coupled to the moving assembly and is movable relative to the platform in response to movement of the moving assembly.

In embodiments, the rebound wall may be coupled to a sensor configured to register a threshold force imparted on the rebound wall and communicate a signal to a controller. The controller may be configured to actuate the first motor to move the rebound wall.

In embodiments, the moving assembly may be configured to pivot the rebound wall between a plurality of orientations. The rebound wall may have at least one of a pitch angle or a yaw angle in each orientation of the plurality of orientations. The at least one of the pitch angle or the yaw angle may be different in each orientation of the plurality of orientations. The dynamic training apparatus may include a second motor fixed to the platform and operatively connected to the moving assembly. The first motor may be configured to pivot the moving assembly to change the pitch angle of the rebound wall relative to the platform. The second motor may be configured to pivot the moving assembly to change the yaw angle of the rebound wall relative to the platform.

In embodiments, the moving assembly may include a hub, a scissor jack, and an arm. The hub may be rotatably coupled to the second motor. The scissor jack may be operatively connected to the first motor and coupled to the hub. The arm may have a first end and a second end. The first end may be fixed to the rebound wall and rotatably supported on the hub. The second end may be pivotably connected to the scissor jack. Upon an actuation of the first motor, the scissor jack may rotate the second end of the arm relative to the first end of the arm to change the pitch angle of the rebound wall relative to the platform.

In embodiments, the scissor jack may include a lead screw operatively connected to the first motor, a first pair of linkages rotatably coupled to the second end of the arm, a second pair of linkages rotatably coupled to the hub, and a coupling member interconnecting the first and second pairs of linkages to one another. The coupling member may be threadingly engaged to the lead screw. The first and second pairs of linkages may be movable, via a rotation of the lead screw, between a plurality of configurations. Each configuration of the plurality of configurations may correspond to a different pitch angle of the rebound wall.

In embodiments, the first end of the arm may support a first nut and a second nut nested with the first nut. The first nut may define a tapered bore therethrough. The hub may include a rod rotatably disposed within the bore such that the arm is rotatable relative to the hub.

In embodiments, the platform may include a base configured to be disposed on ground, and a post extending perpendicularly from the base. The moving assembly may be rotatably supported on the post. The second motor may be fixed to the post and actuatable to enable the rebound wall to rotate between a plurality of yaw angles relative to the post.

In embodiments, the moving assembly may include a rotatable drive shaft operatively connected to the second motor and coupled to the hub such that rotation of the drive shaft rotates the hub relative to the post to change the yaw angle of the rebound wall relative to the post.

In embodiments, the rebound wall may include a rear surface, a front surface, and at least one spinning element. The rear surface may be coupled to the moving assembly. The front surface may be disposed opposite the rear surface and may be planar. The at least one spinning element may be rotatably disposed on the front surface and be adapted to couple to a third motor that spins the at least one spinning element.

In another aspect of the present disclosure, another embodiment of a dynamic training apparatus is provided. The dynamic training apparatus includes a platform, a first motor, and a moving assembly. The moving assembly is coupled to the platform and the first motor. The moving assembly includes a bracket, a hub, an arm, and a scissor jack. The hub is pivotably coupled to the platform. The arm has a first end and a second end. The first end is fixed to the bracket and pivotably coupled to the hub. The scissor jack is pivotably coupled to the second end of the arm and the hub. The scissor jack is coupled to the first motor. The bracket is pivotable relative to the platform in response to an actuation of the scissor jack.

In embodiments, the dynamic training apparatus may include a rebound wall coupled to the bracket. The moving assembly may be configured to pivot the rebound wall relative to the platform to change at least one of a pitch angle or a yaw angle of the rebound wall relative to the platform.

In embodiments, the dynamic training apparatus may include a second motor and a rotatable drive shaft fixed to the platform and operatively coupled to the second motor. The rotatable drive shaft may be rotatably coupled to the hub such that rotation of the drive shaft rotates the hub to change the yaw angle of the rebound wall.

In embodiments, the scissor jack may include a lead screw, a first and second pair of linkages, and a coupling member. The lead screw may be operatively connected to the first motor. The first pair of linkages may be rotatably coupled to the second end of the arm. The second pair of linkages may be rotatably coupled to the hub. The coupling member may interconnect the first and second pairs of linkages and may be threadingly engaged with the lead screw. The first and second pairs of linkages may be movable, via a rotation of the lead screw, between a plurality of configurations. Each configuration of the plurality of configurations may correspond to a different pitch angle of the rebound wall.

In yet another aspect of the present disclosure, a method of operating a dynamic training system is provided. The method includes: actuating a first motor to pivot a rebound wall about a yaw axis to change a yaw angle of the rebound wall; and actuating a second motor to pivot the rebound wall about a pitch axis to change a pitch angle of the rebound wall. The yaw axis extends perpendicular to ground and the pitch axis extends parallel to ground.

In embodiments, the method may include pivoting the rebound wall about at least one of the pitch axis or the yaw axis in response to a threshold force imparted on the rebound wall.

In embodiments, the method may include remotely controlling movement of the rebound wall relative to the platform.

In embodiments, the method may include actuating a scissor jack to move the rebound wall relative to the platform. Actuating the scissor jack may include rotating a lead screw of the scissor jack to one of approximate or space a first and a second pair of linkages relative to one another.

BRIEF DESCRIPTION OF THE DRAWINGS

Embodiments of the present disclosure are described herein with reference to the accompanying drawings, wherein.

DETAILED DESCRIPTION

Embodiments of the presently disclosed dynamic training apparatus and methods of operating the dynamic training apparatus are described in detail with reference to the drawings, in which like reference numerals designate identical or corresponding elements in each of the several views.

As used herein, the terms parallel and perpendicular are understood to include relative configurations that are substantially parallel and substantially perpendicular up to about +/−10 degrees from true parallel and true perpendicular.

Turning to FIGS. 1A-9C, a dynamic training apparatus, in accordance with an embodiment of the present disclosure, is generally designated as 10, and is in the form of a powered dynamic wall configured for rebounding or returning a round object, such as, for example, a tennis ball, upon contact therewith. Dynamic training apparatus 10 includes a platform 100 disposed on a level surface, for example, ground "G," a rebound wall 200, and a motorized moving assembly 300 having a pitch assembly 300a and a yaw assembly 300b. Rebound wall 200 is movably coupled to platform 100 via moving assembly 300. Pitching and yawing assemblies 300a, 300b are configured to selectively move (e.g., pivot/rotate/articulate) rebound wall 200 between a plurality of orientations to change a rebound/return trajectory of a ball that contacts rebound wall 200, as described in greater detail herein.

Figure 1A:
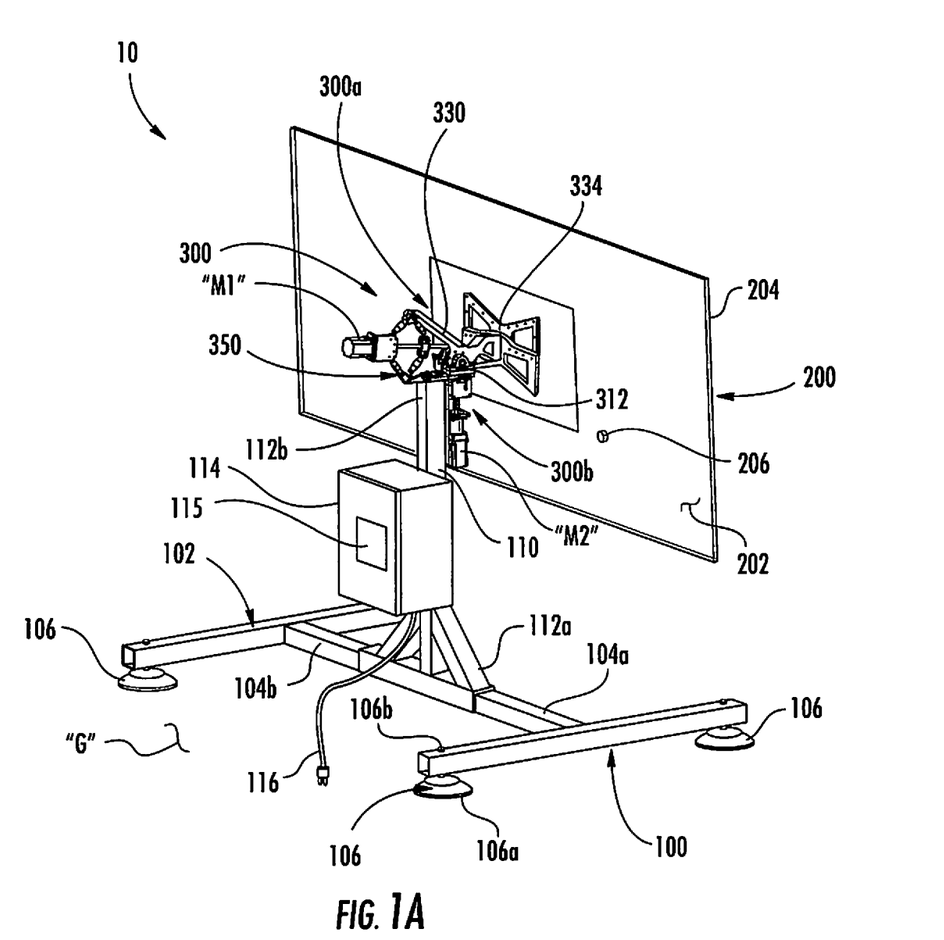
FIG. 1A is a rear, perspective view of a dynamic training apparatus in accordance with an embodiment of the present disclosure.

With reference to FIG. 1A, platform 100 provides a stationary structure that supports rebound wall 200 and moving assembly 300. It is contemplated that platform 100 can be in the form of any stationary support structure suitable for supporting rebound wall 200 and moving assembly 300. Platform 100 includes a base 102 and a post 110 extending perpendicularly from base 102. In some embodiments, base 102 and post 110 are fabricated from materials that exhibit structural integrity and have weight bearing capacity, such as, for example, various metals. Base 102 includes a pair of T-shaped bars 104a, 104b connected to one another to form an I-shaped frame that is configured to be disposed on any suitable level surface, such as, for example, ground "G." It is contemplated that base 102 may be in the form of a monolithically formed I-shaped frame. T-shaped bars 104a, 104b may be axially movable relative to one another and/or post 110 to adjust a center of gravity of platform 100.

Each T-shaped bar 104a, 104b includes a plurality of feet 106 coupled thereto. Each foot of the plurality of feet 106 includes a bottom portion 106a that engages ground "G" and a top portion 106b that secures bottom portion 106a to one of T-shaped bars 104a, 104b. Top portion 106a can be threadingly coupled to one of T-shaped bars 104a, 104b. In embodiments, one or more of the plurality of feet 106 are rotatably coupled to T-shaped bars 104a, 104b such that rotation of any one of the plurality of feet 106 relative to T-shaped bars 104a, 104b raises and/or lowers platform 100 relative to ground "G." It is contemplated that bottom portion 106a may be in the form of suction cups to better secure platform 100 to ground "G." In some embodiments, one or more of the plurality of feet 106 may include wheels (not shown). In some embodiments, the wheels may be motorized (e.g., secured to one or more motors to enable the entire apparatus to move). The motorized wheels permit dynamic training apparatus 10 to roam in a pre-defined area to dynamically change the position of dynamic training apparatus 10 relative to the ground. In further embodiments, feet 106 may include motorized casters.

Post 110 has a first end 112a coupled to a central portion of base 102 and a second end 112b rotatably supporting moving assembly 300 thereon. First end 112a can have any suitable configuration to stabilize post 110 relative to base 102. In embodiments, first end 112a can include a three-pronged configuration. It is contemplated that post 110 can be a solid and/or a hollow tube. Base 102 and post 110 may be integrally connected and/or monolithically formed with one another. In embodiments, base 102 and post 110 can be selectively separable and/or connectable. A cabinet 114 is attached to an intermediate portion of post 110 and houses a controller 115. Controller 115 can be electrically coupled with any suitable electronic component (e.g., circuitry, microchips, switches, cables, etc.) and/or to a power cable 116 (e.g., 110V, 220 V, etc.) configured to be connected to a power source (not shown). Controller 115 is electrically connected to moving assembly 300 to direct the movement of moving assembly 300 and, in turn, rebound wall 200. In embodiments, controller 115 can be battery operated.

Figure 1B:
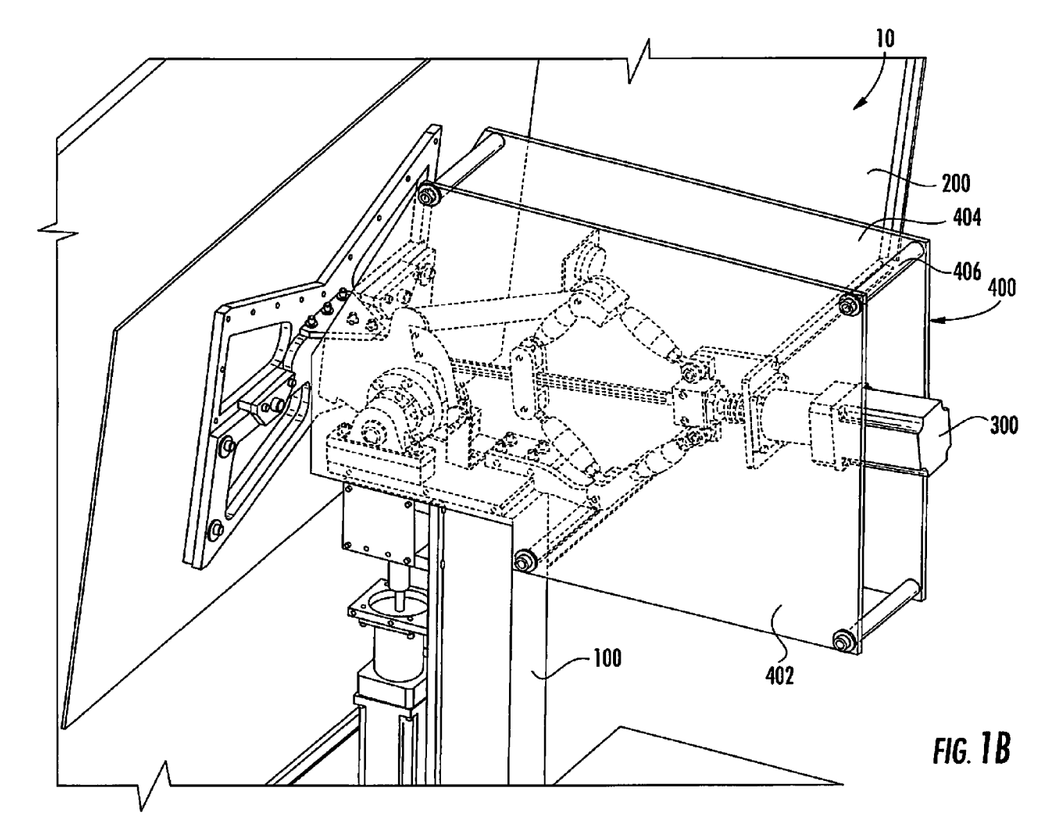
FIG. 1B is an enlarged, rear perspective view of the dynamic training apparatus of FIG. 1A with a housing secured thereto.

As shown in FIG. 1B, dynamic training apparatus 10 includes a housing 400 that partially or wholly covers moving assembly 300 for protecting moving assembly 300. Housing 400 includes walls 402, 404 that are secured together by a plurality of fasteners 406. Walls 402, 404 can be formed of any suitable material, such as, for example, PMMA, and can have any suitable shape and/or dimension. In some embodiments, walls 402, 404 may include any protective barrier, such as, for example, fencing and/or the like. Housing 400 may include a cut-off switch (not shown).

Figure 2:
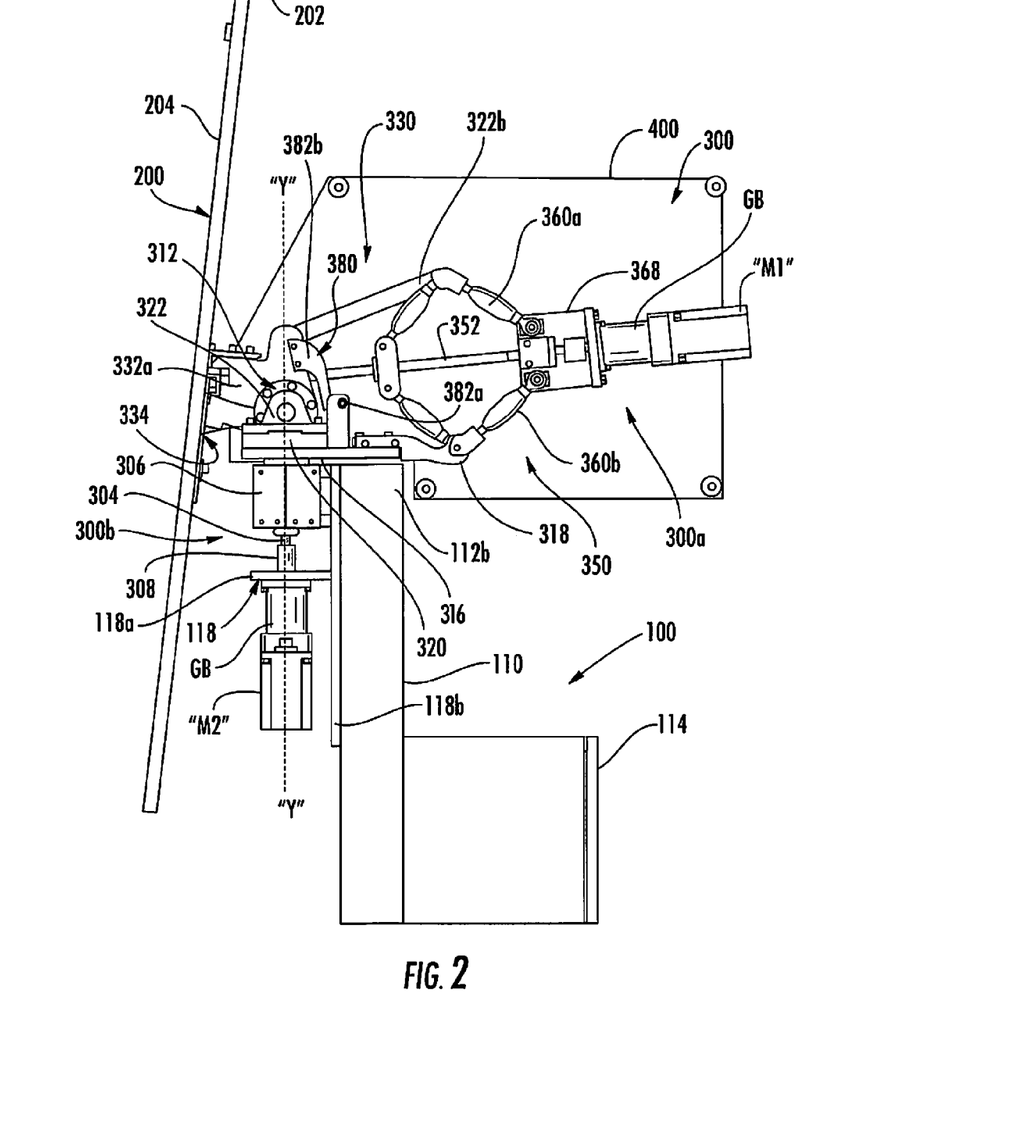
FIG. 2 is an enlarged side view of a portion of the dynamic training apparatus shown in FIG. 1B with a portion of the housing removed for clarity.

With reference to FIGS. 1A and 2, rebound wall 200 is movable (e.g., pivotable/articulatable/rotatable) relative to platform 100 in response to movement of pitching and yawing assemblies 300a, 300b of moving assembly 300, as will be described in greater detail below. Rebound wall 200 has a rectangular and planar configuration. Rebound wall 200 may have any suitable configuration. For example, rebound wall 200 can be oval, arcuate, triangular, square, concave, convex, tapered, undulating, variable, polygonal, uniform, non-uniform, and/or oblong. Rebound wall 200 has a rear surface 202 coupled to moving assembly 300 and a planar front surface 204. Rebound wall 200, or portions thereof, is made of any suitable metallic, polymeric, and/or like material. Front surface 204 is configured to deflect/return/rebound a moving projectile (e.g., a tennis ball) that contacts/impacts front surface 204. It is contemplated that front surface 204 can be configured to deflect the moving projectile at a velocity substantially equal to a pre-impact velocity thereof.

In embodiments, rebound wall 200 is configured to pivot/articulate/rotate in response to a threshold force imparted on rebound wall 200. Rear surface 202 and/or front surface 204 may include a sensor 206 (or a plurality of sensors) coupled thereto. Sensor 206 is electrically and/or wirelessly connected to controller 115 and is configured to detect when the threshold force is imparted on rebound wall 200. Upon sensing the threshold force (e.g., contact with a tennis ball), sensor 206 communicates with controller 115 and controller 115 directs moving assembly 300 to move, thereby carrying out a pre-selected change in orientation of rebound wall 200. It is contemplated that dynamic training apparatus 10 may include a plurality of sensors that can be disposed on or in various components of dynamic training apparatus 10, such as, moving assembly 300. In embodiments, controller 115 may be configured to carry out a random change in orientation of rebound wall 200.

Figure 3:
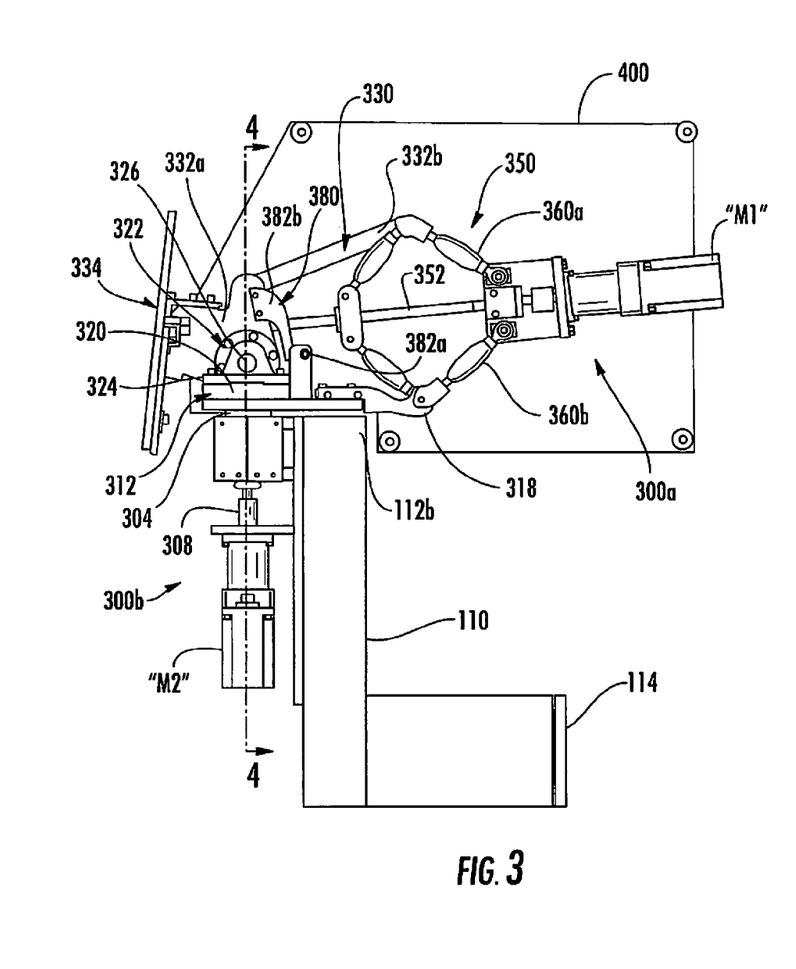
FIG. 3 is a side view of the dynamic training apparatus shown in FIG. 2, with a rebound wall removed therefrom.
Figure 4:
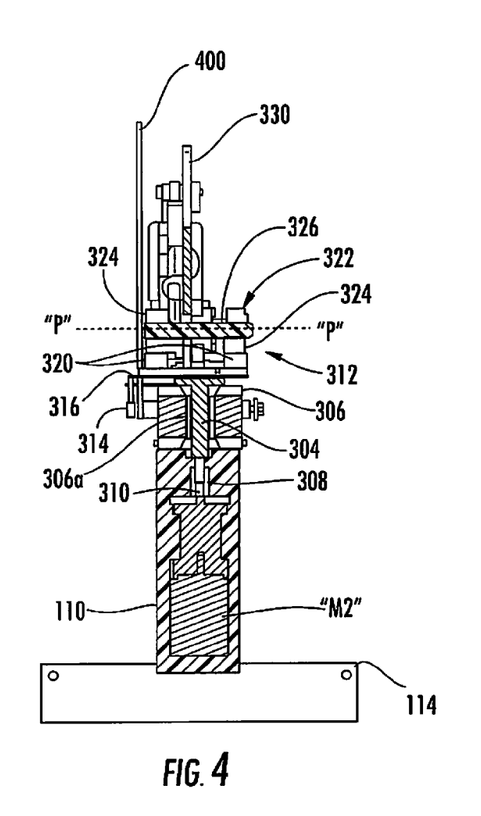
FIG. 4 is a cross-sectional view of the dynamic training apparatus as taken along line 4-4 of FIG. 3.

With reference to FIGS. 2-4, dynamic training apparatus 10 includes a first motor "M1" and a second motor "M2" each operatively connected to moving assembly 300 to drive movement of moving assembly 300 between a plurality of orientations relative to platform 100. Motors "M1," "M2" may include any suitable motor, such as, for example, stepper motors, servomotors, or other electric and/or gas powered motors. In some embodiments, motors "M1," "M2" may be in the form of stepper motors configured to produce one revolution per every 50 steps. In embodiments, one or both motors "M1," "M2" can be configured to produce any number of revolutions per any number of steps. Motors "M1" and/or "M2" can include a gear box "GB" that provides any suitable gearing ratio.

First motor "M1" is operatively coupled to a proximal end of pitch assembly 300a to drive movement of rebound wall 200 relative to a pitch axis "P" (FIG. 4) defined through moving assembly 300. Pitch axis "P" extends parallel to base 102 and rebound wall 200. Second motor "M2" is operatively coupled to yaw assembly 300b and is fixed to post 110 of platform 100 via a horizontal plate 118a of a mount 118. Second motor "M2" drives movement of rebound wall 200 relative to a yaw axis "Y" (FIG. 2) defined through moving assembly 300. Yaw axis "Y" extends perpendicular to base 102 and parallel to post 110. Pitch and yaw axes "P" and "Y" may be oriented in perpendicular relation to one another such that rebound wall 200 is movable relative to platform 100 between a plurality of orientations in response to movement of pitching and/or yawing assemblies 300a, 300b of moving assembly 300. Rebound wall 200 has a different pitch angle and/or yaw angle in each orientation of the plurality of orientations, as described in greater detail below.

With continued reference to FIGS. 2-4, yaw assembly 300b includes a rotatable drive shaft 304 that extends from second motor "M2" to a hub 312. Drive shaft 304 extends through a thrust bearing box 306 fixed to a vertical plate 118b of mount 118. Thrust bearing box 306 includes a thrust bearing 306a that facilitates rotation of pitch assembly 300a relative to yaw assembly 300b as drive shaft 304 rotates rebound wall 200. A coupling or rigid sleeve 308 surrounds drive shaft 304 and a shaft 310 of second motor "M2" to drivingly connect drive shaft 304 to second motor "M2."

Figure 6A:
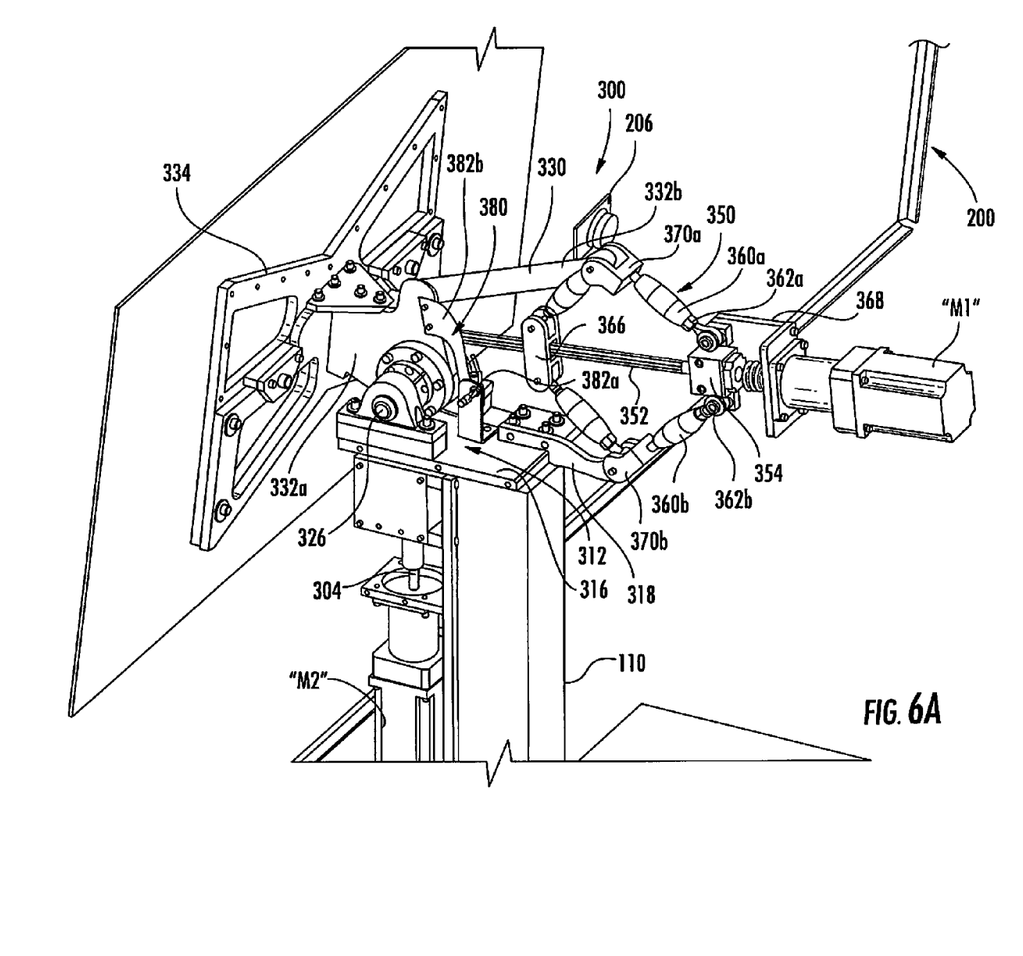
FIG. 6A is an enlarged, right, rear perspective view of the dynamic training apparatus shown in FIG. 1A.
Figure 6B:
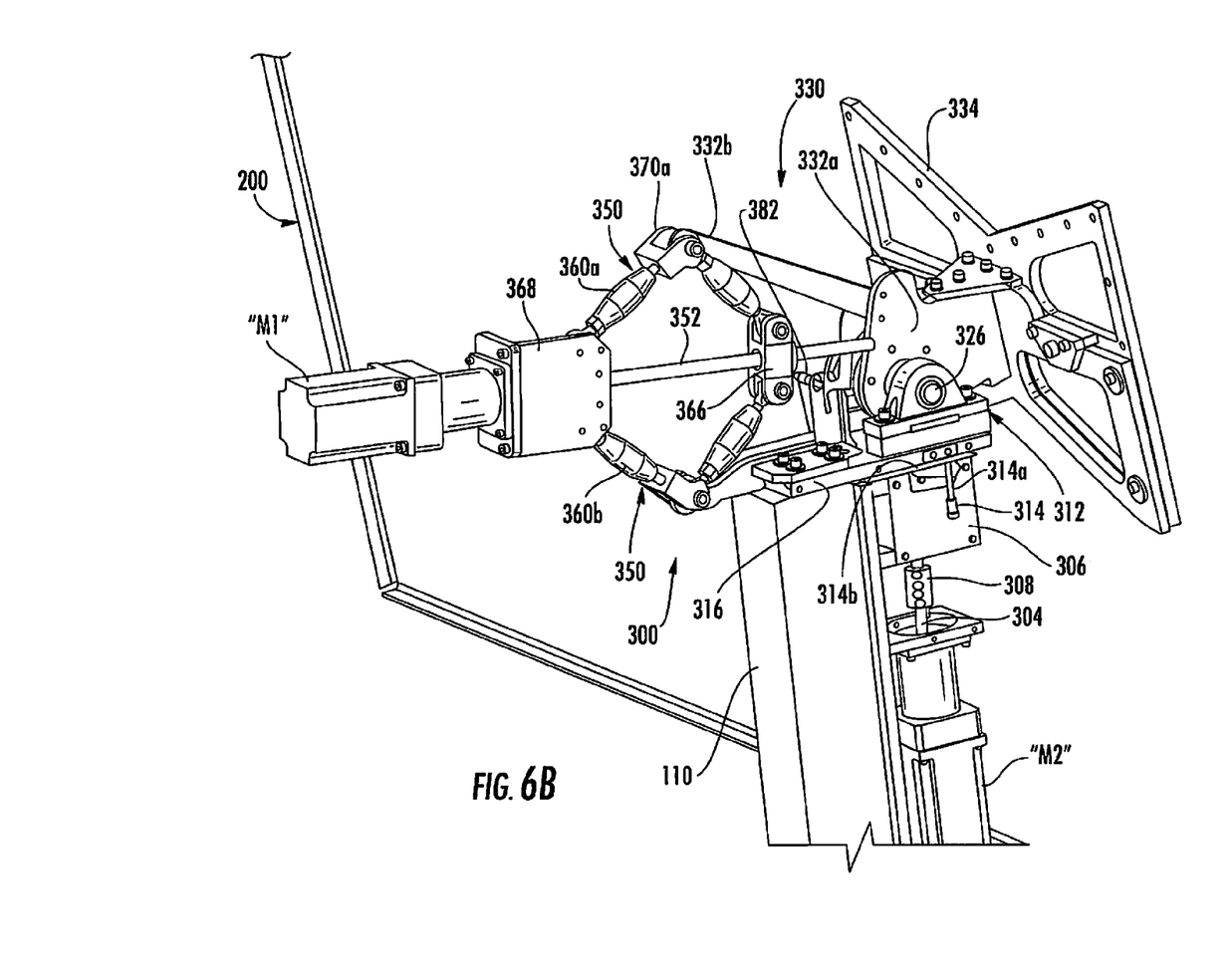
FIG. 6B is an enlarged, left, rear perspective view of the dynamic training apparatus shown in FIG. 1A.

As seen in FIG. 6B, yaw assembly 300b includes a yawing indicator 314 connected to hub 312 that is configured to detect the yaw angle of rebound wall 200 and communicate the detected yaw angle to controller 115. Yawing indicator 314 includes a fixed portion 314a fixedly mounted to thrust bearing box 306 and a moving portion 314b secured to a plate 316 of pitch assembly 300a. Moving portion 314b rotates with pitch assembly 300a about yaw axis "Y" relative to fixed portion 314a. Yawing indicator 314 can be electrically coupled to controller 115 (FIG. 1A) and can include any number of, and/or type of, sensor (e.g., electrical, optical, magnetic, etc.) secured to fixed and/or moving portions 314a, 314b. Yawing indicator 314 can be configured to initiate an auto-shut off, for example, if rebound wall 200 rotates beyond a predetermined yaw angle.

Referring to FIGS. 2-4, pitch assembly 300a includes hub 312, an arm 330, and a scissor jack assembly 350. Hub 312 includes a plate 316, an extension 318, a pair of spacers 320 and an axle assembly 322. Plate 316 is fixed to drive shaft 304 of yaw assembly 300b and rotatable therewith. Extension 318 is fixed to plate 316 and extends in a proximal direction relative to plate 316. Extension 318 is rotatably coupled to a portion of scissor jack assembly 350, as described in greater detail below. Spacers, such as, for example, blocks 320, are supported on plate 316 in spaced relation to one another to balance axle assembly 322. In embodiments, blocks 320 are fabricated from a resilient material, such as, for example, rubber, to absorb shock exerted on hub 312 from movement of moving assembly 300.

Axle assembly 322 includes a pair of spaced apart supports 324 fixedly supported on respective blocks 320 and spaced from plate 316. Axle assembly 322 includes an axle or rod 326 extending through supports 324 and rotatable therein. Axle 326 defines pitch axis "P" therethrough.

With reference to FIGS. 2-4, 5A, 5B, 6A, and 6B, arm 330 is rotatably coupled to axle 326 of hub 312. Arm 330 has a first end 332a fixed to a bracket 334 that is secured to rebound wall 200 and a second end 332b that is pivotably connected to scissor jack assembly 350. Arm 330 may have a straight or linear configuration. In some embodiments, arm 330 may be variously configured, such as, for example, L-shaped, hooked, V-shaped, arcuate, or other suitable configurations. Bracket 334 has a butterfly configuration and is mounted on rear surface 202 of rebound wall 200 to fix first end 332a of arm 330 to rebound wall 200. In some embodiments, bracket 334 may be variously configured, such as, for example, those alternatives described herein.

Figures 5A, 5B:
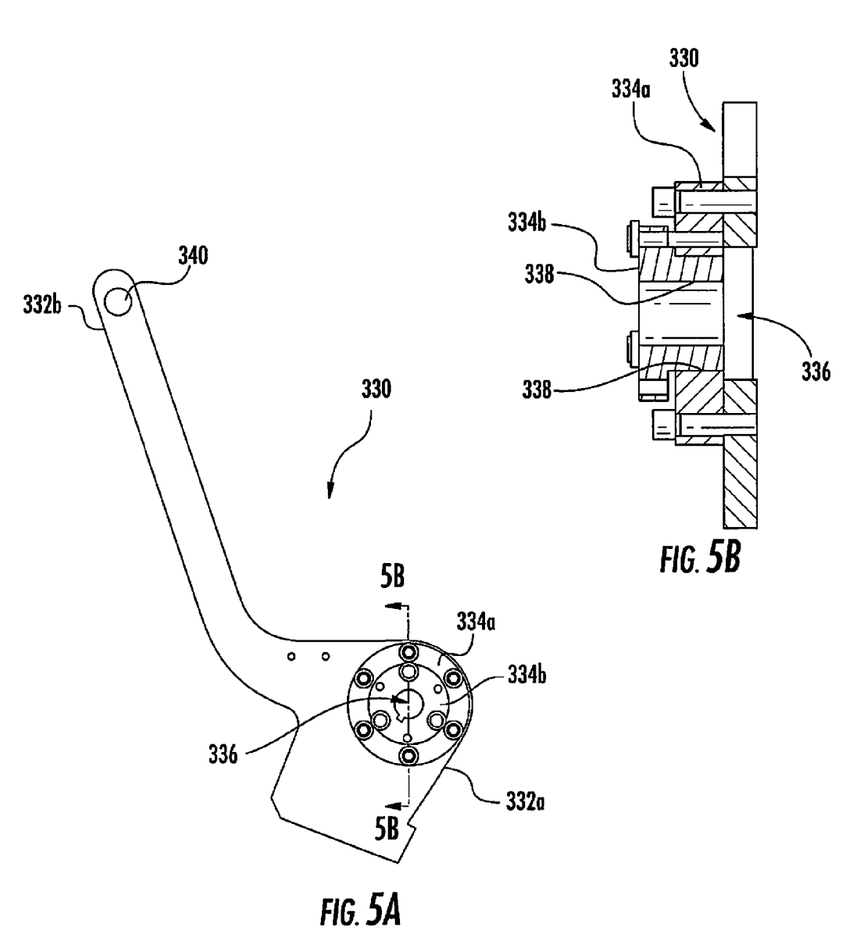
FIG. 5A is a plan view of an arm of a moving assembly of the dynamic training apparatus shown in FIG. 1A.
FIG. 5B is a cross-sectional view of the arm taken along line 5B-5B of FIG. 5A.

With specific reference to FIGS. 5A and 5B, first end 332a of arm 330 includes a first nut 334a and a second nut 334b nested with first nut 334a, or concentrically disposed therein. First nut 334a defines a bore 336 therethrough having a tapered portion 338 configured to facilitate securement of second nut 334b within first nut 334a. Second nut 334b may be in the form of a split-squeeze compression nut. With brief reference to FIG. 3, axle 326 is rotatably disposed within bore 336 such that arm 330 is rotatable relative to hub 312. Referring again to FIG. 5A, second end 332b of arm 330 defines a bore 340 therethrough that pivotably supports a first pair of linkages 352a (see FIG. 6A) of scissor jack assembly 350 therein. Scissor jack assembly 350 transfers and converts power provided by first motor "M1" to second end 332b of arm 330 to rotate second end 332b of arm 330 relative to first end 332a of arm 330, which results in a change in the pitch angle of rebound wall 200, as described in greater detail below.

Figure 7:
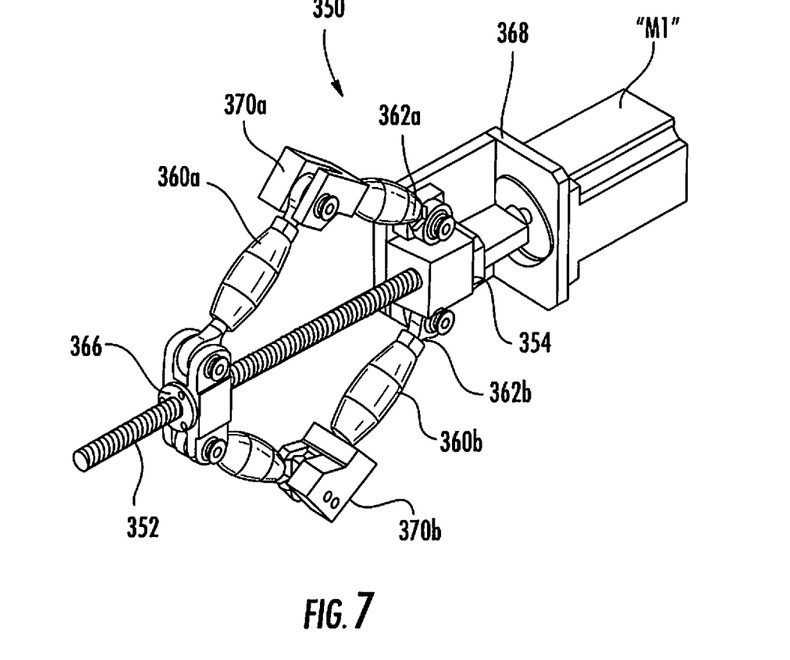
FIG. 7 is a perspective view of components of the moving assembly of the dynamic training apparatus shown in FIG. 1A.

With reference to FIGS. 6A, 6B, and 7, scissor jack assembly 350 is operatively connected to first motor "M1" and coupled between hub 312 and second end 332b of arm 330. Scissor jack assembly 350 includes a lead screw 352, a first and second pair of linkages 360a, 360b, and a coupling member 366. Lead screw 352 is drivingly connected to first motor "M1." Lead screw 352 is coupled to first motor "M1" via a coupling box 354 that supports a bearing (not shown) inside. In some embodiments, lead screw 352 may be a ball screw. In some embodiments, lead screw has a Teflon® coated thread form. Lead screw 352 is threadingly connected to coupling member 366 such that rotation of lead screw 352 causes coupling member 366 to translate relative to, and along, lead screw 352.

First and second pairs of linkages 360a, 360b each include proximal ends 362a, 362b. Proximal ends 362a, 362b each include an eyebolt with a bearing rotatably supported on an L-shaped bracket or mount 368, upon which first motor "M1" is also mounted. Mount 368 provides a pivot point about which proximal ends 362a, 362b of first and second pairs of linkages 360a, 360b pivot. First pair of linkages 360a are pivotably interconnected at a joint thereof 370a. Joint 370a is pivotably connected to second end 332b of arm 330. Second pair of linkages 360b are interconnected at a joint 370b thereof. Joint 370b is pivotably connected to extension 318 of hub 312. Joints 370a, 370b of respective first and second pairs of linkages 360a, 360b can be approximated or distanced from one another, via a rotation of lead screw 352, between second end 332b of arm 330 and extension 318 of hub 312. Each change in configuration of first and second pairs of linkages 360a, 360b, via relative movement of joints 370a, 370b, corresponds to a different pitch angle of rebound wall 200, as described in greater detail below.

Pitch assembly 300a includes a pitching indicator 380 configured to detect the pitch angle of rebound wall 200. Pitching indicator has a first member 382a fixed to plate 316 and a second member 382b mounted to arm 330. Second member 382b is movable with arm 330 relative to first member 382a. Pitching indicator 380 can be electrically coupled to controller 115 (FIG. 1A) and can include any number of, and/or type of, sensor (e.g., electrical, optical, magnetic, etc.) secured to first and/or second member 382a, 382b. Pitching indicator 380 can be configured to initiate an auto-shut off, for example, if rebound wall 200 moves beyond a predetermined pitch angle.

Figure 8A:
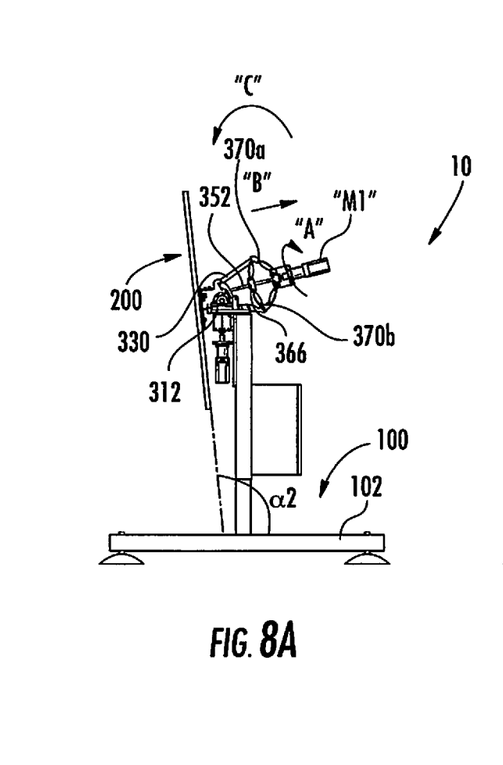
FIGS. 8A-8C are progressive side views of the dynamic training apparatus shown in FIG. 1A illustrating a plurality of pitch angles of the rebound wall.
Figure 8B:
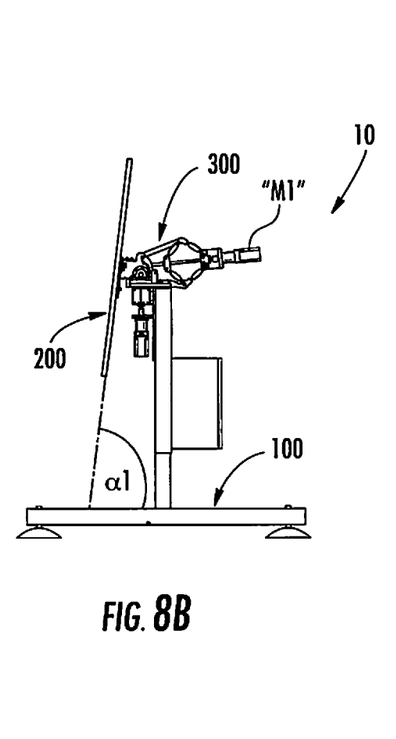
Figure 8C:
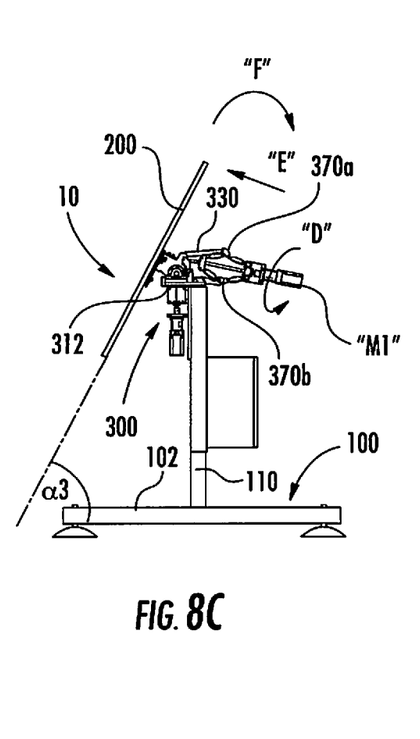

In operation, with reference to FIGS. 8A-8C, pitch assembly 300a is actuated to change a pitch angle of rebound wall 200. Specifically, an actuation of first motor "M1" drives a rotation of lead screw 352 of scissor jack assembly 350, in a direction (e.g., clockwise and/or counterclockwise) indicated by arrow "A" in FIG. 8A, to move coupling member 366 of scissor jack assembly 350 in a direction indicated by arrow "B" in FIG. 8A. As coupling member 366 is moved proximally along lead screw 352, joints 370a, 370b of scissor jack assembly 350 expand outwardly relative to one another to rotate second end 332b of arm 330 about pitch axis "P," in the direction indicated by arrow "C" in FIG. 8A, and away from hub 312. As can be appreciated, the relative movement of joints 370a, 370b of scissor jack assembly 350 also rotates scissor jack assembly 350 and first motor "M1" relative to hub 312. Rebound wall 200 pivots, in response to the rotation of arm 330, to change the pitch angle of rebound wall 200 from pitch angle "α1" (FIG. 8B) to pitch angle "α2" (FIG. 8A). Continued rotation of arm 330 moves rebound wall 200 between a plurality of pitch angles.

To pivot rebound wall 200 in an opposite direction from that discussed above, first motor "M1" is actuated to rotate lead screw 352, in a direction indicated by arrow "D" (e.g. clockwise and/or counterclockwise) in FIG. 8C, to move coupling member 366 of scissor jack assembly 350 in a direction indicated by arrow "E" in FIG. 8C. As coupling member 366 is moved distally along lead screw 352, joints 370a, 370b of scissor jack assembly 350 are approximated, causing a rotation of second end 332b of arm 330 about pitch axis "P," in the direction indicated by arrow "F" in FIG. 8C, and towards hub 312. Rebound wall 200 pivots, in response to the rotation of arm 330 to change the pitch angle of rebound wall 200 from pitch angle "α1" (FIG. 8B) to pitch angle "α3" (FIG. 8C).

Figure 9A:
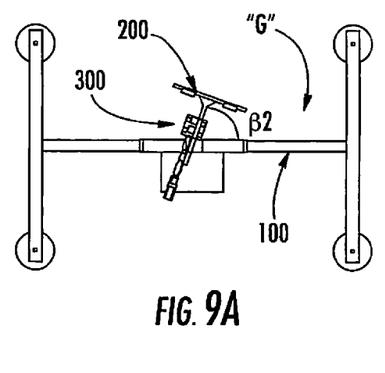
FIGS. 9A-9C are progressive top views of the dynamic training apparatus shown in FIG. 1A illustrating a plurality of yaw angles of the rebound wall.
Figure 9B:
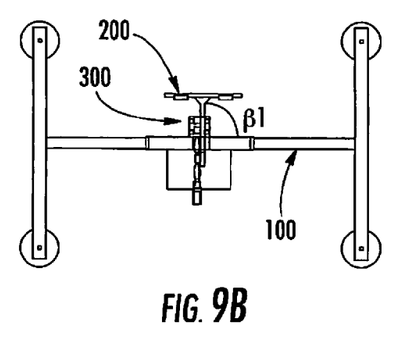
Figure 9C:
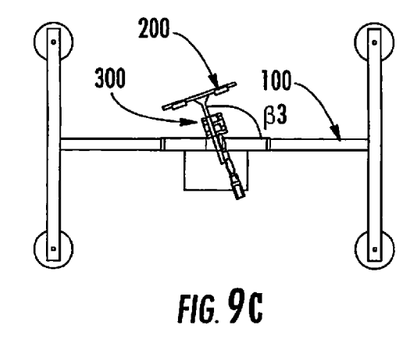

With reference to FIGS. 9A-9C, an operation of dynamic training apparatus 10 may include changing the yaw angle of rebound wall 200 from a yaw angle "β1" (FIG. 9B) to a yaw angle "β2" (FIG. 9A) via actuation of yaw assembly 300b. To change the yaw angle of rebound wall 200, second motor "M2" is actuated to rotate drive shaft 304 relative thereto and, in turn, rotating hub 312 of pitch assembly 300a relative to yaw assembly 300b about yaw axis "Y." A rotation of hub 312 results in the concomitant rotation of rebound wall 200 relative to yaw assembly 300b and platform 100, in the direction indicated by arrow "G" in FIG. 9A. The yaw angle "β3" of rebound wall 200 shown in FIG. 9C can be achieved by second motor "M2" reversing the rotational direction of drive shaft 304.

It is contemplated that both the pitch angle and the yaw angle may be simultaneously adjusted and at various rates of speed during operation of dynamic training apparatus 10. It is contemplated that only one of the pitch angle and the yaw angle may be adjusted during operation of dynamic training apparatus 10.

In embodiments, dynamic training apparatus 10 may be provided with a communication device, such as, for example, a mobile device (including an application "app" on the mobile device), a laptop, a remote controller, a joystick or the like for controlling movement of rebound wall 200 through remote and/or direct communication with controller 115. For example, any suitable communication device can be electrically coupled to controller 115 and/or wirelessly connected to controller 115 via acoustic, electromagnetic, Wi-Fi, ZigBee, wireless LAN, DECT, GSM, UWB, UMTS, Bluetooth, sonic or radio frequency. In embodiments, dynamic training apparatus 10 can be coupled to a timer to enable rebound wall 200 to pivot/articulate/rotate at predetermined intervals/times.

In use, a user, e.g., an athletic trainer, can input a command into communication device to control the orientation of rebound wall 200. In some embodiments, dynamic training apparatus 10 may be preprogrammed to move rebound wall 200 between a plurality of selected orientations and at a preselected rate of speed. It is contemplated that dynamic training apparatus 10 includes software the carries out the selected movements of rebound wall 200.

Figure 10:
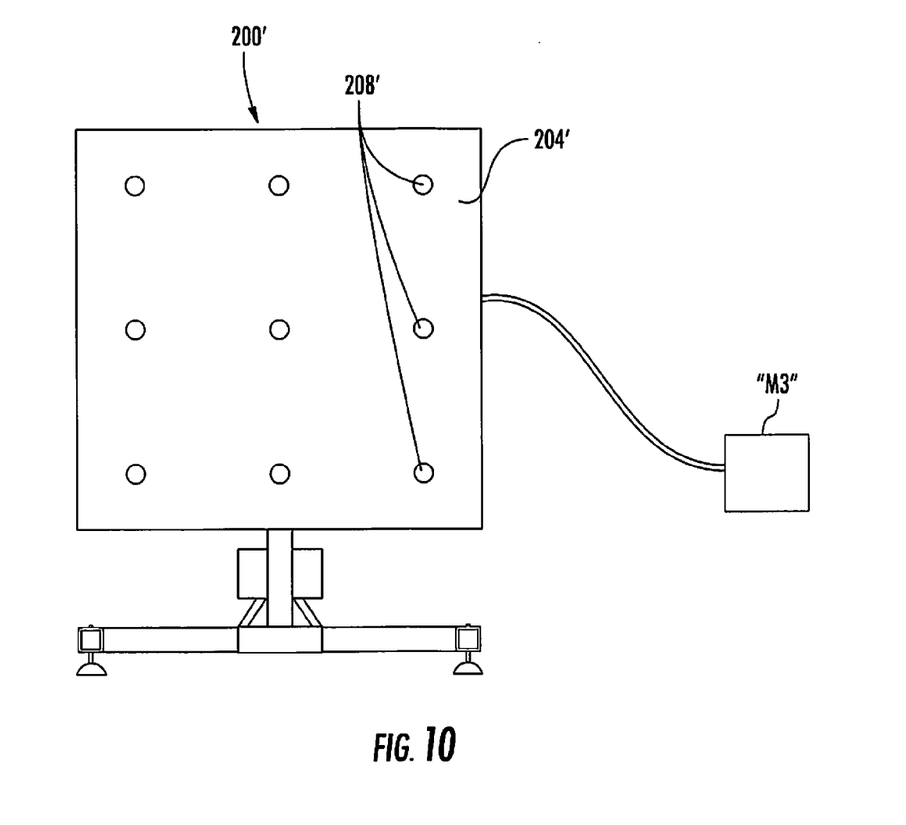
FIG. 10 is a schematic view of an alternative embodiment of a rebound wall connected to a motor in accordance with the principles of the present disclosure.

With reference to FIG. 10, an alternative embodiment of a rebound wall 200', similar to rebound wall 200 discussed above, is provided. Rebound wall 200' includes one or a plurality of globular objects and/or spinning elements 208' (e.g., discs). Spinning elements 208' are rotatably disposed within a front surface 204' of rebound wall 200'. A portion of each spinning element 208' may protrude from front surface 204'. In some embodiments, spinning elements 208' are motorized by a motor "M3" such that spinning elements 208' can be rotated at one or more selected rotational velocities. In use, as a round object (e.g., a tennis ball) makes contact with one of spinning elements 208', spinning elements 208' induce a spin (i.e., English) to the round object to alter its course.

Any of the components described herein may be fabricated from either metals, plastics, resins, composites or the like taking into consideration strength, durability, wearability, weight, resistance to corrosion, ease of manufacturing, cost of manufacturing, and the like.

It is contemplated that any of the components described herein may be connected using any suitable fastening technique, such as, for example, welding, crimping, molding, etc. As can be appreciated, any of the components can be connected using adhesives, rivets, screws, bolts, nails, etc.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with one or more of the embodiments may be combined with the elements and features of one or more of the other embodiments without departing from the scope of the present disclosure, and that such modifications and variations are also included within the scope of the present disclosure. Accordingly, the subject matter of the present disclosure is not limited by what has been particularly shown and described.

The invention claimed is:

1. A dynamic training apparatus, comprising:
   a platform;
   a first motor;
   a moving assembly coupled to the platform and the first motor, the moving assembly being movable in response to an actuation of the first motor and including:
      an extension having a first end coupled to the platform and a second end;
      an arm having a first end rotatably coupled to the platform and a second end; and
      a scissor jack operatively coupled to the first motor and having a first joint connected to the second end of the arm, and a second joint connected to the second end of the extension; and
   a rebound wall coupled to the first end of the arm of the moving assembly, wherein upon an actuation of the first motor, the scissor jack rotates the second end of the arm about a pivot axis defined through the first end of the arm to move the rebound wall relative to the platform and further including a second motor fixed to the platform and operatively connected to the moving assembly, the first motor being configured to pivot the moving assembly to change the pitch angle of the rebound wall relative to the platform and the second motor being configured to pivot the moving assembly to change the yaw angle of the rebound wall relative to the platform.

2. The dynamic training apparatus according to claim 1, wherein the moving assembly is configured to pivot the rebound wall between a plurality of orientations, the rebound wall having at least one of a pitch angle or a yaw angle in each orientation of the plurality of orientations, the at least one of the pitch angle or the yaw angle being different in each orientation of the plurality of orientations.

3. The dynamic training apparatus according to claim 1, wherein the moving assembly further includes a hub rotatably supported on the platform and operatively coupled to the second motor such that actuation of the second motor effects a rotation of the hub relative to the platform, the first end of the extension being connected to the hub.

4. The dynamic training apparatus according to claim 3, wherein the scissor jack includes:
   a lead screw operatively connected to the first motor;
   a first pair of linkages rotatably coupled to the second end of the arm and rotatably connected to one another via the first joint;
   a second pair of linkages rotatably coupled to the second end of the extension and rotatably connected to one another via the second joint; and
   a coupling member interconnecting the first and second pairs of linkages to one another and being threadingly engaged to the lead screw, the first and second pairs of linkages being movable, via a rotation of the lead screw, between a plurality of configurations, wherein each configuration of the plurality of configurations corresponds to a different pitch angle of the rebound wall.

5. The dynamic training apparatus according to claim 3, wherein the platform includes:
   a base configured to be disposed on ground; and
   a post extending perpendicularly from the base, wherein the moving assembly is rotatably supported on the post.

6. The dynamic training apparatus according to claim 5, wherein the second motor is fixed to the post and actuatable to enable the rebound wall to rotate between a plurality of yaw angles relative to the post.

7. The dynamic training apparatus according to claim 6, wherein the moving assembly further includes a rotatable drive shaft, the rotatable drive shaft operatively connected to the second motor and the hub such that rotation of the drive shaft rotates the hub relative to the post to change the yaw angle of the rebound wall relative to the post.

8. The dynamic training apparatus according to claim 3, wherein the first end of the arm supports a first nut and a second nut nested with the first nut, the first nut defining a tapered bore therethrough, the hub further including a rod rotatably disposed within the bore such that the arm is rotatable relative to the hub.

9. The dynamic training apparatus according to claim 1, wherein the rebound wall includes:
   a rear surface coupled to the moving assembly;
   a front surface disposed opposite the rear surface, the front surface being planar; and
   at least one spinning element rotatably disposed on the front surface, the at least one spinning element adapted to couple to a third motor that spins the at least one spinning element.

10. The dynamic training apparatus according to claim 1, wherein the rebound wall is coupled to a sensor configured to register a threshold force imparted on the rebound wall and communicate a signal to a controller, the controller configured to actuate the first motor to move the rebound wall.

11. A dynamic training apparatus, comprising:
    a platform;
    a first motor; and
    a moving assembly coupled to the platform and the first motor, the moving assembly including:
       a bracket having a rebound wall attached thereto;
       a hub pivotably coupled to the platform;
       an arm having a first end and a second end, the first end being fixed to the bracket and pivotably coupled to the hub; and
       a scissor jack pivotably coupled to the second end of the arm and the hub and being operatively coupled to the first motor, wherein the bracket is pivotable relative to the platform in response to an actuation of the scissor jack wherein the moving assembly is configured to pivot the rebound wall relative to the platform to change at least one of a pitch angle or a yaw angle of the rebound wall relative to the platform and further including a second motor; and a rotatable drive shaft coupled to the platform and operatively coupled to the second motor, the rotatable drive shaft being operatively coupled to the hub such that rotation of the drive shaft rotates the hub to change the yaw angle of the rebound wall.

12. The dynamic training apparatus according to claim 11, wherein the scissor jack includes:
    a lead screw operatively connected to the first motor;
    a first pair of linkages rotatably coupled to the second end of the arm;
    a second pair of linkages rotatably coupled to the hub; and
    a coupling member interconnecting the first and second pairs of linkages and being threadingly engaged with the lead screw, the first and second pairs of linkages being movable, via a rotation of the lead screw, between a plurality of configurations, wherein each configuration of the plurality of configurations corresponds to a different pitch angle of the rebound wall, wherein the lead screw of the scissor jack pivots relative to the platform in response to an actuation of the scissor jack.

13. A method of operating a dynamic training system utilizing the device of claim 1
    actuating a first motor to pivot a rebound wall about a yaw axis to change a yaw angle of the rebound wall, the yaw axis extending perpendicular to ground; and
    actuating a second motor to pivot the rebound wall about a pitch axis to change a pitch angle of the rebound wall, the pitch axis extending parallel to ground.

14. The method according to claim 13, further including pivoting the rebound wall about at least one of the pitch axis or the yaw axis in response to a threshold force imparted on the rebound wall.

15. The method according to claim 13, further including remotely controlling movement of the rebound wall relative to the platform.

16. The method according to claim 13, further including actuating a scissor jack to move the rebound wall relative to the platform.

17. The method according to claim 13, wherein actuating the scissor jack includes rotating a lead screw of the scissor jack to one of approximate or space a first and a second pair of linkages of the scissor jack relative to one another.

* * * * *